US009980911B2

(12) United States Patent
Barnett et al.

(10) Patent No.: US 9,980,911 B2
(45) Date of Patent: *May 29, 2018

(54) BIOERODIBLE SILICON-BASED COMPOSITIONS FOR DELIVERY OF THERAPEUTIC AGENTS

(71) Applicants: pSivida US, Inc., Watertown, MA (US); pSiMedica Limited, Malvern (GB)

(72) Inventors: Christian Barnett, Pershore (GB); Paul Ashton, Newton, MA (US); Leigh T. Canham, Malvern (GB)

(73) Assignee: PSIVIDA US, INC., Watertown, MA (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/143,283

(22) Filed: Apr. 29, 2016

(65) Prior Publication Data

US 2017/0049703 A1 Feb. 23, 2017

Related U.S. Application Data

(63) Continuation of application No. 14/211,170, filed on Mar. 14, 2014, now Pat. No. 9,603,801.

(60) Provisional application No. 61/798,324, filed on Mar. 15, 2013.

(51) Int. Cl.
| | |
|---|---|
| *A61K 9/14* | (2006.01) |
| *A61K 38/42* | (2006.01) |
| *A61K 9/19* | (2006.01) |
| *A61K 9/50* | (2006.01) |
| *A61K 9/00* | (2006.01) |
| *A61K 39/395* | (2006.01) |
| *C07K 16/22* | (2006.01) |

(52) U.S. Cl.
CPC ............ *A61K 9/146* (2013.01); *A61K 9/0048* (2013.01); *A61K 9/0051* (2013.01); *A61K 9/143* (2013.01); *A61K 9/145* (2013.01); *A61K 9/19* (2013.01); *A61K 9/5031* (2013.01); *A61K 38/42* (2013.01); *A61K 39/3955* (2013.01); *A61K 39/39591* (2013.01); *C07K 16/22* (2013.01); *C07K 2317/24* (2013.01)

(58) Field of Classification Search
CPC ... A61K 9/0048; A61K 9/146; A61K 39/3955
See application file for complete search history.

(56) References Cited

U.S. PATENT DOCUMENTS

| | | | |
|---|---|---|---|
| 3,832,458 A | 8/1974 | Merrill | |
| 3,919,060 A | 11/1975 | Pogge et al. | |
| 3,919,723 A | 11/1975 | Heimke et al. | |
| 4,036,979 A | 7/1977 | Asato | |
| 4,608,048 A | 8/1986 | Cortese et al. | |
| 4,772,203 A | 9/1988 | Scheunemann | |
| 4,793,825 A | 12/1988 | Benjamin et al. | |
| 5,057,082 A | 10/1991 | Burchette, Jr. | |
| 5,370,630 A | 12/1994 | Smidebush et al. | |
| 5,558,071 A | 9/1996 | Ward et al. | |
| 5,591,453 A | 1/1997 | Ducheyne et al. | |
| 5,665,114 A | 9/1997 | Weadock et al. | |
| 5,665,428 A | 9/1997 | Cha et al. | |
| 5,792,099 A | 8/1998 | DeCamp et al. | |
| 5,797,898 A | 8/1998 | Santini, Jr. et al. | |
| 5,807,574 A | 9/1998 | Cheskin et al. | |
| 5,874,109 A | 2/1999 | Ducheyne et al. | |
| 5,922,299 A | 7/1999 | Bruinsma et al. | |
| 6,060,036 A | 5/2000 | Armini | |
| 6,086,908 A | 7/2000 | Gopferich | |
| 6,238,705 B1 | 5/2001 | Liu et al. | |
| 6,322,895 B1 | 11/2001 | Canham | |
| 6,521,284 B1 | 2/2003 | Parsons et al. | |
| 6,579,851 B2 | 6/2003 | Goeke et al. | |
| 6,666,214 B2 | 12/2003 | Canham | |
| 6,696,258 B1 | 2/2004 | Wei et al. | |
| 6,770,480 B1 | 8/2004 | Canham | |
| 6,929,950 B2 | 8/2005 | Canham et al. | |
| 7,090,681 B2 | 8/2006 | Weber et al. | |
| 7,332,339 B2 | 2/2008 | Canham | |
| 7,375,168 B2 | 5/2008 | Zhang et al. | |
| 7,433,811 B2 | 10/2008 | Gao et al. | |

(Continued)

FOREIGN PATENT DOCUMENTS

| | | |
|---|---|---|
| EP | 0092708 A2 | 11/1983 |
| EP | 0178769 A2 | 4/1986 |

(Continued)

OTHER PUBLICATIONS

Extended European Search Report for Application No. 14779965.4 (PCT/US2014/024362), dated Jul. 8, 2016.
Supplementary European Search Report for Application No. 14767541.7 (PCT/US2014/025612), dated Aug. 4, 2016.
Amorij et al., "Development of stable influenza vaccine powder formulations challenges and possibilities." Pharmaceutical Research, 25(6):1261 (2008).
Analogue (http://dictionary.reference.com/browse/analogue?s=t) accessed Nov. 25, 2015, pg. 1.
Anglin et al., "Porous Silicon in Drug Delivery Devices and Materials," Advanced Drug Delivery Reviews, 60:1266-1277 (2008).

(Continued)

*Primary Examiner* — Gina C Justice
(74) *Attorney, Agent, or Firm* — Hogan Lovells US LLP

(57) ABSTRACT

The invention comprises a composition comprising a bioerodible porous silicon-based carrier material wherein the carrier material carries at least one large molecule therapeutic agent and at least one amorphous sugar, optionally further comprising a crystallization inhibitor. The composition may be used in vitro or in vivo to deliver the therapeutic agent, preferably in a controlled fashion over an intended period of time such as over multiple days, weeks or months. The composition may be used for treating or preventing conditions of a patient such as chronic diseases.

20 Claims, 3 Drawing Sheets

(56) References Cited

U.S. PATENT DOCUMENTS

| | | | |
|---|---|---|---|
| 7,563,451 B2 | 7/2009 | Lin et al. | |
| 7,585,521 B2 | 9/2009 | Barbe et al. | |
| 7,713,778 B2 | 5/2010 | Li et al. | |
| 7,763,277 B1 | 7/2010 | Canham et al. | |
| 8,097,236 B2 | 1/2012 | Aston et al. | |
| 8,128,912 B2 | 3/2012 | Canham et al. | |
| 8,147,864 B2 | 4/2012 | Canham et al. | |
| 8,303,975 B2 | 11/2012 | Canham et al. | |
| 8,313,761 B2 | 11/2012 | Canham et al. | |
| 8,318,194 B2 | 11/2012 | Canham et al. | |
| 8,361,491 B2 | 1/2013 | Canham et al. | |
| 8,461,129 B2 | 6/2013 | Bolduc et al. | |
| 8,623,399 B2 | 1/2014 | Canham et al. | |
| 9,023,896 B2 | 5/2015 | Ashton et al. | |
| 9,205,051 B2 | 12/2015 | Canham et al. | |
| 9,603,801 B2 * | 3/2017 | Barnett | A61K 9/143 |
| 2002/0034646 A1 | 3/2002 | Canham | |
| 2004/0052867 A1 | 3/2004 | Canham | |
| 2004/0166140 A1 | 8/2004 | Santini et al. | |
| 2004/0170694 A1 | 9/2004 | Colic | |
| 2006/0067979 A1 | 3/2006 | Kunzler et al. | |
| 2006/0154069 A1 | 7/2006 | Lin et al. | |
| 2006/0269893 A1 | 11/2006 | Aloise et al. | |
| 2007/0042046 A1 | 2/2007 | Saffie et al. | |
| 2007/0071787 A1 | 3/2007 | Saffie et al. | |
| 2008/0057101 A1 | 3/2008 | Roorda | |
| 2008/0241242 A1 | 10/2008 | Caruso et al. | |
| 2009/0137688 A1 | 5/2009 | Yang | |
| 2009/0208556 A1 | 8/2009 | Freeman et al. | |
| 2010/0196435 A1 | 8/2010 | Freeman et al. | |
| 2010/0278931 A1 | 11/2010 | Ashton et al. | |
| 2011/0028412 A1 | 2/2011 | Cappello et al. | |
| 2011/0052657 A1 | 3/2011 | Canham et al. | |
| 2011/0052659 A1 | 3/2011 | Canham et al. | |
| 2011/0182967 A1 | 7/2011 | Canham et al. | |
| 2011/0217353 A1 | 9/2011 | Canham et al. | |
| 2011/0217354 A1 | 9/2011 | Canham et al. | |
| 2011/0236493 A1 | 9/2011 | Canham et al. | |
| 2012/0177695 A1 | 7/2012 | Ashton et al. | |
| 2012/0207682 A1 | 8/2012 | Ashton | |
| 2013/0041004 A1 | 2/2013 | Drager et al. | |
| 2013/0053794 A1 | 2/2013 | Cadden et al. | |
| 2013/0084243 A1 | 4/2013 | Goetsch et al. | |
| 2013/0096073 A1 | 4/2013 | Sidelman | |
| 2013/0115186 A1 | 5/2013 | Baecker et al. | |
| 2014/0065221 A1 | 3/2014 | Eloy et al. | |
| 2014/0271764 A1 | 9/2014 | Ashton et al. | |

FOREIGN PATENT DOCUMENTS

| | | |
|---|---|---|
| EP | 1776949 A2 | 4/2007 |
| JP | 59101145 | 6/1984 |
| JP | 59131346 | 7/1984 |
| JP | 9-506869 | 7/1997 |
| JP | 10175994 A | 6/1998 |
| JP | 2007091716 A | 4/2007 |
| JP | 200913035 A | 1/2009 |
| JP | 2010228986 A | 10/2010 |
| WO | WO-1990/11070 A1 | 10/1990 |
| WO | WO-1992/05777 A1 | 4/1992 |
| WO | WO-1994/21314 A1 | 9/1994 |
| WO | WO-1997/06101 A1 | 2/1997 |
| WO | WO-1997/32570 A1 | 9/1997 |
| WO | WO-1998/00107 A2 | 1/1998 |
| WO | WO-99/36357 A1 | 7/1999 |
| WO | WO-1999/39746 A2 | 8/1999 |
| WO | WO-1999/53898 A1 | 10/1999 |
| WO | WO-2000/005339 A1 | 2/2000 |
| WO | WO-2000/38655 A1 | 7/2000 |
| WO | WO-01/028529 A1 | 4/2001 |
| WO | WO-01/28587 A2 | 4/2001 |
| WO | WO-01/032760 A1 | 5/2001 |
| WO | WO-2001/062232 A1 | 8/2001 |
| WO | WO-2001/062235 A2 | 8/2001 |
| WO | WO-01/76564 A1 | 10/2001 |
| WO | WO-02/096389 A1 | 12/2002 |
| WO | WO-2004/071949 A2 | 8/2004 |
| WO | WO-2005/051358 A1 | 6/2005 |
| WO | WO-2006/037160 A1 | 4/2006 |
| WO | WO-2006/050221 A2 | 5/2006 |
| WO | WO-2006/0067979 A1 | 6/2006 |
| WO | WO-2007/106868 A2 | 9/2007 |
| WO | WO-2007/115261 A2 | 10/2007 |
| WO | WO-2009/009563 A2 | 1/2009 |
| WO | WO-2010/038068 A1 | 4/2010 |
| WO | WO-2010/090596 A1 | 8/2010 |
| WO | WO-2010/096733 A2 | 8/2010 |
| WO | WO-2010/111627 A1 | 9/2010 |
| WO | WO-2010/129545 A2 | 11/2010 |
| WO | WO-2012/046009 A1 | 4/2012 |
| WO | 2012-061377 A1 | 5/2012 |
| WO | WO-2012/061377 A1 | 5/2012 |
| WO | WO-2012/088306 A2 | 6/2012 |

OTHER PUBLICATIONS

Bourges, J.L. et al. "Intraocular implants for extended drug delivery: Therapeutic applications" Advanced Drug Delivery Reviews 2006, 58, 1182-1202.

Canham, "Porous Silicon as a Therapeutic Biomaterial," 1st Annual International IEEE-EMBS Special Topic Conference on Microtechnologies in medicine & Biology, Oct. 12-14, 2000, Lyon, France.

Cheng et al., "Intravitreal properties of porous silicon photonic crystals: a potential self-reporting intraocular drug delivery vehicle," Br. J. Ophthalmology, 92:705-711 (2008).

Cohen et al., "Microfabrication of Silicon-Based Nanoporous Particulates for Medical Applications," Biomedical Microdevices, 5(3):253-259 (2003).

Corticotropin (https://web.archive.org/web/20111223224129/http://www.drugs.com/monograph/corticotropin-antiinflammatory.html), accessed Dec. 23, 2011, pp. 1-10.

Corticotropin Pubchem (https://pubchem.ncbi.nlm.nih.gov/compound/16132265#section=Top) accessed Nov. 25, 2015, p. 1.

Gordon et al., "Present status of corticotropin (ACTH), cortisone, and hydrocortisone in ophthalmology," Brit J Ophthalmol, 37:85-98 (1953).

Haghjou, N. et al. "Sustained Release Intraocular Drug Delivery Devices for Treatment of Uveitis" Journal of Ophthalmic and Vision Research 2011; vol. 6, No. 4, pp. 317-329.

International Preliminary Examination Report and Written Opinion dated May 7, 2013 for PCT/US2011/058774 (CDSI-114-WO1).

International Search Report dated Jan. 26, 2011, Serial No. PCT/US2010/033541 (CDSI-106-WO1).

Jarvis, K. et al., "Porous Silicon—A Nanostructured Delivery System," International Conference on Nanoscience and Nanotechnology,IEEE, 536-539 (2006).

Knott, M. "We have the technology . . . —The ultimate science-fiction wedding may be on early the next century when carbon life forms and silicon sensors get hitched," New Scientist, 51:2075, 36-39 (1997).

Kumar, D.S. et al., "Nanostructured Porous Silicon—A Novel Biomaterial for Drug Delivery," International Journal of Pharmacy and Pharmaceutical Sciences, 1(2):8-16 (2009).

Low, S. et al., "The biocompatibility of porous silicon in tissues of the eye," Biomaterials, 30:2873-2880 (2009).

Mastropaolo et al., "Crystal and molecular structure of paclitaxel (taxol)," Proc Natl Acad Sci USA, 92:6920-4 (1995).

Matthews Coefficient calculator, retrieved from http://csb.wfu.edu/tools/vmcalc/vm.html. Accessed Oct. 29, 2015.

Mazzobre et al., "Protective role trehalose on thermal stability of lactase in relation to its glass crystal forming properties and effect of delaying crystallization," Lebensm. Wiss. U. Technol. 30, 324-9 (1997).

Prestidge et al., "Mesoporous silicon: a platform for the delivery of therapeutics," Expert Opinion Drug Deliv., 4(2): 101-110 (2007).

Sachdev et al., "Evolution of bevacizumab-based therapy in the management of breast cancer," Clin Breast Cancer, 8(5):402-10 (2008).

(56) References Cited

OTHER PUBLICATIONS

Sinakten depo. "Suspenziya dlya vnutrimyshechnogo wedeniya 1mg/ml, ampula 1ml, 1-12 pachka kartonnaya 1, N2 P N013438/ 01," Sep. 30, 2005, Novartis Pharma, Nycomed Austria, [online], [retrieved on Jun. 26, 2014]. Retrieved from the internet <URL: http://www.rlsnet.ru/prep_index_id_59990.htm >, p. 1 (with machine translation).

Tetracosactide (http://www.drugs.com/international/tetracosactide.html) accessed Nov. 18, 2015, pp. 1-3.

Vadia et al., "Mesoporous material, MCM-41: A new drug carrier," Asian Journal of Pharmaceutical and Clinical Research, 4(2): 44-53 (2011).

Vinegoni et al., "Porous silicon microcavities," Silicon-Based Materials and Devices, 2:1-134 (2000).

Heikkila, et al., "Evaluation of Mesoporous TCPSi, MCM-41, SBA-15, and TUD-1 Materials as API Carriers for Oral Drug Delivery," Drug Delivery, 14: 337-347 (2007).

Supplementary European Search Report dated Oct. 11, 2016 for EP 11 83 8672.

Andrew et al., "Sustained Release of a Monoclonal Antibody from Electrochemically Prepared Mesoporous Silicon Oxide," Advanced Functional Materials, 20(23): 4168-4174 (2010).

Slowing et al., "Mesoporous Silica Nanoparticles as Controlled Release Drug Delivery and Gene Transfection Carriers," Advanced Drug Delivery Reviews, 60(11): 1278-1288 (2008).

Eriksson et al., "Investigations into the stabilization of drugs by sugar glasses: I. Tablets prepared from stabilized alkaline phosphatase," International Journal of Pharmaceuticals, 249 (2002) pp. 39-70.

Hinrichs et al., "Inulin glasses for the stabilization of therapeutic proteins," International Journal of Pharmaceuticals, 215 (2001) pp. 163-174.

Schebor et al., "Glassy State and Thermal Inactivation of Invertase and Lactase in Dried Amorphous Matrices," Biotechnol. Prog. 1997, No. 13, pp. 857-863.

Chinese Office Action dated Oct. 23, 2017 in Chinese Application No. 2016-501894 (with English language translation).

\* cited by examiner

BIOERODIBLE SILICON-BASED COMPOSITIONS FOR DELIVERY OF THERAPEUTIC AGENTS

RELATED APPLICATIONS

This application in a continuation of U.S. patent application Ser. No. 14/211,170, filed Mar. 14, 2014, which claims the benefit of priority to U.S. Provisional Patent Application Ser. No. 61/798,324, filed Mar. 15, 2013, the contents of each of which are hereby incorporated by reference herein in their entirety.

BACKGROUND

There has been considerable interest within the pharmaceutical industry in the development of dosage forms which provide controlled release of therapeutic agents over a period of time. Releasing an active substance in this way can help to improve bioavailability and ensure that appropriate concentrations of the agent are provided for a sustained period without the need for repeated dosing. In turn, this also helps to minimize the effects of patient non-compliance which is frequently an issue with other forms of administration.

Patients may be reluctant to comply with their treatment regime, as compliance may be painful and traumatic. For example, today there exist therapeutic agents that can treat, with good clinical success, ophthalmic conditions, such as age-related macular degeneration, diabetic macular edema, diabetic retinopathy, choroidal neovascularization, and other conditions that can lead to blindness or near blindness. Often the afflicted population is an older patient group who must adjust their activities of daily living to cope with the early stages of these diseases. However, as the disease progresses, permanent eye damage occurs and many clinically effective treatments are only preventative, and not restorative. Thus, consistent compliance to the treatment regime is nearly mandatory to prevent loss of sight.

Unfortunately, treatment regimens typically require the patient to hold still while the physician pierces the patient's eye with a hypodermic needle to deliver the therapeutic agent into the eye, typically the vitreous of the eye. This can be traumatic and painful and accordingly a patient may be reluctant to receive the injections. The ability to provide a longer-term benefit for each injection, and thus reduce the pain and trauma suffered by the patient, turns on the required pharmacokinetics of the therapeutic agent and the delivery vehicle that carries and releases the agent.

Some known delivery vehicles have active ingredients that are incorporated into polymer and sol-gel systems by entrapment during synthesis of the matrix phase. Microencapsulation techniques for biodegradable polymers include such methods as film casting, molding, spray drying, extrusion, melt dispersion, interfacial deposition, phase separation by emulsification and solvent evaporation, air suspension coating, pan coating and in-situ polymerization. Melt dispersion techniques are described, for example, in U.S. Pat. Nos. 5,807,574 and 5,665,428.

In an alternative approach, the active ingredient is loaded after formation of the porous matrix is complete. Such carrier systems generally have micron-sized rather than nanometer-sized pores to allow the agents to enter into the pores. U.S. Pat. No. 6,238,705, for example, describes the loading of macroporous polymer compositions by simple soaking in a solution of the active ingredient and U.S. Pat. Nos. 5,665,114 and 6,521,284 disclose the use of pressure to load the pores of implantable prostheses made of polytetrafluoroethene (PTFE). While this approach may be effective for small organic molecules, larger molecules such as proteins tend to aggregate in large pores and do not effectively release in vivo in a controlled manner.

With smaller pores, it has proved difficult to incorporate high concentrations of therapeutic agents due to blocking of the narrow pores. Deposition of material towards the opening of the pores tends to prevent a high proportion of the material from occupying the pore system. The problem of achieving high loading of the active ingredient limits the effectiveness of many currently known delivery systems.

Another concern when delivering therapeutic agents through an delivery vehicle is the biocompatibility of the delivery vehicle following release of the drug. Bioerodible or resorbable delivery vehicle materials would be an attractive alternative to delivery vehicles that require removal following release of the drug. The design and preparation of bioerodable delivery vehicles for carrying therapeutic agents has begun to be explored. PCT Publication No. WO2009/009563 describes a drug delivery system comprising a porous silicon material.

Therefore, there remains a continuing need for the development of improved dosage forms for the controlled release of therapeutic agents, which are biocompatible and are capable of delivering large molecules in a sustained fashion.

SUMMARY

The invention comprises a composition comprising a bioerodible porous silicon-based carrier material wherein the carrier material carries at least one large molecule therapeutic agent and at least one amorphous sugar, optionally further comprising a crystallization inhibitor. In certain embodiments, the composition is prepared using vacuum-assisted flash drying.

The disclosed compositions are for delivering therapeutic agents, particularly large molecules such as proteins, peptides, antibodies, carbohydrates, polymers, vaccines, small interfering RNA (siRNA) or polynucleotides, in a controlled manner. The compositions comprise a porous silicon-based carrier material loaded with the therapeutic agent and an amorphous sugar. In some embodiments, the compositions comprise a porous silicon-based carrier material loaded with the therapeutic agent and a mixture of amorphous sugars. In some embodiments, the compositions comprise a porous silicon-based carrier material loaded with the therapeutic agent, and a mixture of a sugar and a crystallization inhibitor. The compositions may be used in vitro or in vivo to deliver the therapeutic agent, preferably in a controlled fashion over an intended period of time such as over multiple days, weeks or months. The carrier material is preferably formed from a bioerodible or resorbable material, e.g., a silicon-based material such as elemental silicon or silicon dioxide, such that removal following release of the therapeutic agent is unnecessary. In certain such embodiments, the carrier material and its breakdown products are biocompatible such that the biological side-effects from the bioerosion of the carrier material are minimal or innocuous.

In certain embodiments, the carrier material comprises porous silicon dioxide, such as mesoporous silicon dioxide. The average pore size of the carrier material is typically selected so that it may carry the therapeutic agent, and example pore sizes are from 2-50 nm in diameter, such as from about 15 to about 40 nm in diameter, from about 20 to about 30 nm in diameter, from about 2 to about 15 nm in diameter, or about 5 to about 10 nm in diameter. Silicon-based materials are also disclosed in U.S. 20120177695, which is incorporated herein by reference.

In certain embodiments, the therapeutic agent is a protein with a molecular weight between about 500 amu and about 200,000 amu, and maybe about 800 amu and about 200,000 amu, about 1000 amu and about 200,000 amu, about 1500 amu and about 200,000 amu, about 2,000 amu and about 200,000, about 5,000 amu and about 200,000 amu, about about 10,000 to about 150,000 amu, between about 10,000 and about 50,000 amu, between about 50,000 and about 100,000 amu or between about 100,000 and about 200,000 amu.

The size of a therapeutic agent may alternatively be characterized by the molecular radius, which may be determined, for example, through X-ray crystallographic analysis or by hydrodynamic radius. The therapeutic agent may be a protein, e.g., with a molecular radius selected from 0.5 nm to 20 nm, such as about 0.5 nm to 10 nm, even from about 1 to 8 nm. Preferably, a suitable pore radius to allow access to particular agents, e.g., proteins, is selected according to a pore-therapeutic agent (agent) differential, defined herein as the difference between the radius of a agent and a radius of a pore. For example, the pore-agent differential for insulin, with a hydrodynamic radius of 1.3 nm and a pore with a minimum radius of 4.8 nm has a pore-protein differential of 3.5 nm. A pore-agent differential may be used to determine minimum suitable average pore size for accommodating a protein of a particular radius. The pore-protein differential may typically be selected from about 3.0 to about 5.0 nm.

Typically the compositions are selected to have an average pore size to accommodate the therapeutic agent. The average pore size of the carrier material may be chosen based on the molecular weight or the molecular radius of the therapeutic agent to be loaded into the pores of the carrier material. For example, a therapeutic agent of molecular weight selected from 100,000 to 200,000 amu may be used with a carrier material of larger average pore size such as from about 15 nm to about 40 nm. In certain embodiments, a therapeutic agent of molecular weight selected from 5,000 to 50,000 amu may be used with a carrier material of smaller average pore size such as from about 2 nm to about 10 nm.

In certain embodiments, the sugars, whether used alone or in combination, are selected from sucrose, fructose, glucose, erythritol, maltitol, lactitol, sorbitol, mannitol, xylitol, D-tagatose, trehalose, trehalose dehydrate, galactose, glycerol, rhamnose, cyclodextrin, raffinose, ribulose, ribose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, glucosamine, mannosamine, fucose, glucuronic acid, gluconic acid, glucono-lactone, abequose, galactosamine, xylo-oligosaccharides, gentio-oligoscaccharides, galacto-oligosaccharides, sorbose, nigero-oligosaccharides, fructooligosaccharides, maltotetraol, maltotriol, maltodextrin, malto-oligosaccharides, lactulose, melibiose, or any combinations thereof. In preferred embodiments, the sugar is selected from trehalose, trehalose dihydrate, sucrose, mannitol, sorbitol, xylitol or glycerol, or a combination thereof.

In certain embodiments, the compositions are prepared by forming the porous carrier material first and then loading the pores with the therapeutic agent, and the amorphous or solution form of the sugar, or a plurality of sugars, or a combination of a sugar and a crystallization inhibitor. In preferred embodiments, the therapeutic agent is loaded before the amorphous or solution form of the sugar or the crystallization inhibitor.

The invention includes methods for loading a therapeutic agent into the pore of a porous silicon-based carrier material, comprising contacting a porous silicon-based carrier material with a therapeutic agent. One exemplary method for loading a therapeutic agent into the pore of a porous silicon-based carrier material comprises selecting a porous silicon-based carrier having pore sizes dimensionally adapted to allow a single protein to load into the pore such that opposite sides of the protein engage opposite sides of the pore. One method for loading a therapeutic agent into the pore of a porous silicon-based carrier material comprises selecting a porous silicon-based carrier having pore sizes dimensionally adapted to admit only a single agent into the width of a single pore at one time (i.e., longitudinal series along the length of a pore are not excluded), e.g., two agents could not be accommodated if positioned side-by-side (laterally) within a pore. Methods for loading an agent into the pore of a silicon-based material and for selecting appropriate carrier materials for an agent of interest are also disclosed in U.S. 20120177695, which is incorporated herein by reference.

The compositions may be disposed on the skin or on the surface of the eye. Alternatively, the compositions may be disposed within the body of a mammal, such as within the eye of a patient, or within any other tissue or organ of the patient's body. In particular applications, the compositions are disposed subcutaneously, subconjunctivally or in the vitreous of the eye. The compositions may be used for treating or preventing conditions of a patient such as chronic diseases. In certain embodiments, the compositions are for treating or preventing diseases of the eye such as glaucoma, macular degeneration, diabetic macular edema and age-related macular degeneration. The therapeutic agent may be released in a controlled manner over a period of weeks or months, for example, to treat or prevent diseases of the eye such as macular degeneration.

The invention comprises stabilized formulations comprising amorphous sugars and methods of stabilizing therapeutic agents in a porous carrier material as described herein. In certain embodiments, the invention comprises stabilized biomolecules, such as antibodies, in the pores of the carrier material such that the half-life or the shelf life of the biomolecule is superior to the half-life or shelf life of the biomolecule outside of the carrier material. In certain embodiments, the proteins of the stabilized formulations are stable to drying under reduced pressure at room temperature ambient conditions. In certain embodiments, the porous carrier material comprising a therapeutic agent and an amorphous sugar is coated with a polymer. In preferred embodiments, the porous carrier material comprising a therapeutic agent and an amorphous sugar is coated with a controlled release polymer.

In certain embodiments of compositions as described herein, the amorphous forms of sugars of the compositions described herein, when in contact with the porous carrier materials described herein, retain their amorphous character at 25° C./60% relative humidity after 90 days than under similar conditions without the porous carrier materials. In certain embodiments, the amorphous sugars stabilize biomolecules, e.g., antibodies, at the temperature of 25° C. for at least 15 days, at least 1 month, at least 6 months, at least 1 year, at least 1.5 years, at least 2 years, at least 2.5 years, at least 3 years or at least 4 years.

In some embodiments, the stabilized formulations of the invention are stable when exposed to non-aqueous solvent such as dichloromethane, or any solvent not capable of solubilizing the sugar.

DETAILED DESCRIPTION

OVERVIEW

Figure 1:
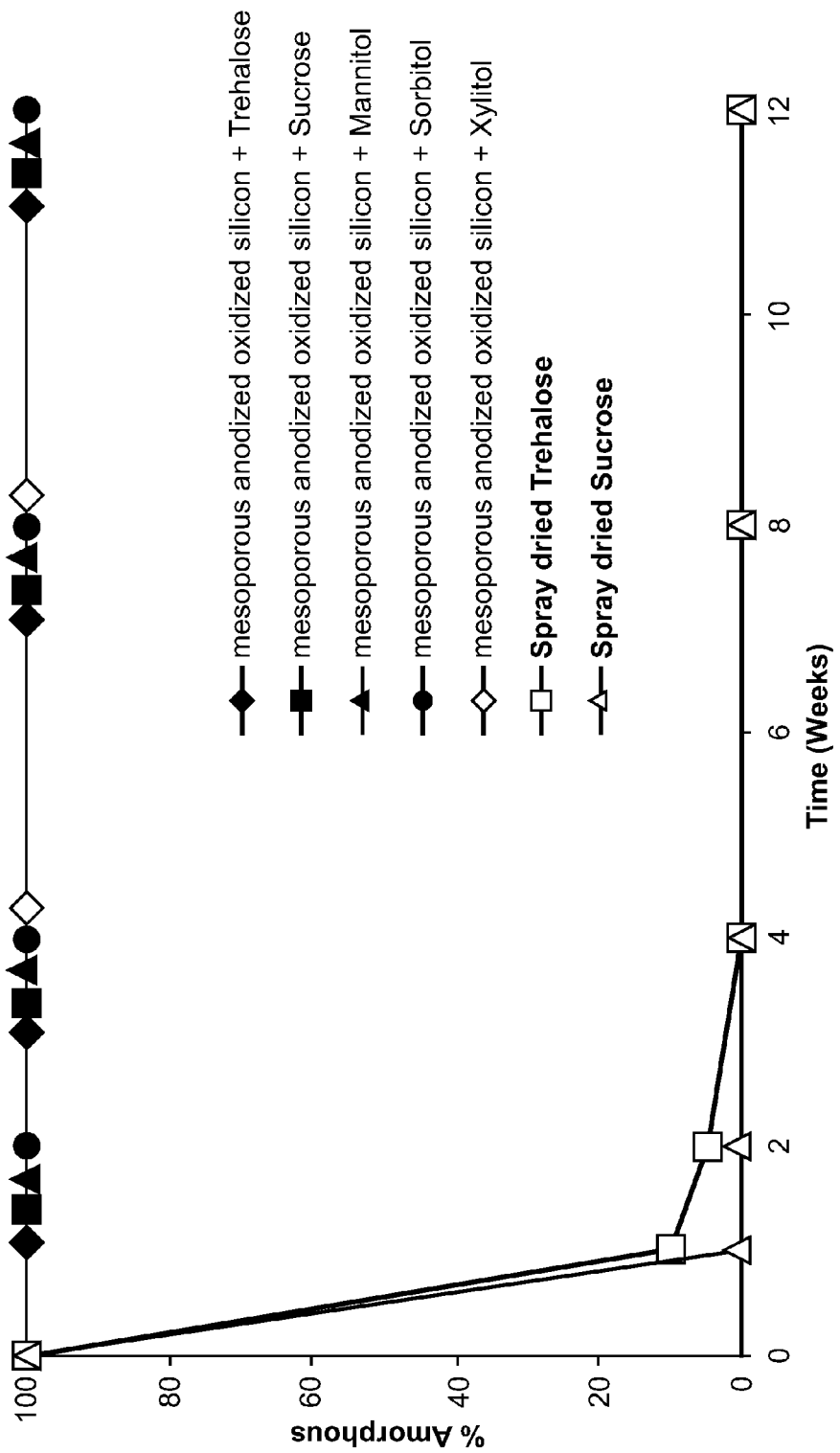
FIG. 1 shows the stabilisation of the amorphous sugars in mesoporous oxidized anodized silicon (e.g., as prepared by Examples 1-3) for 90 days at 25° C. and 60% relative humidity.

Sustained and controlled delivery of therapeutic agents to patients, particularly patients with chronic conditions such as glaucoma or cancer, is becoming increasingly important in modern medical therapy. Many therapies are most effective when administered at frequent intervals to maintain a near constant presence of the active agent within the body. While frequent administration may be recommended, the inconvenience and associated difficulty of patient compliance may effectively prevent treatment in this manner. As a result, sustained release compositions that release therapeutic agents in a controlled manner are very attractive in fields such as cancer therapy and treatment of other chronic diseases.

Compositions that release therapeutic agents in vivo or in vitro may be formed from a variety of biocompatible or at least substantially biocompatible materials. One type of composition employs a silicon-based carrier material. Silicon-based carrier materials may include, for example, elemental silicon, and oxidized silicon in forms such as silicon dioxide (silica), or silicates. Some silicon-based compositions have demonstrated high biocompatibility and beneficial degradation in biological systems, eliminating the need to remove the carrier material following release of the therapeutic agent.

Tests show that high porosity silicon-based materials, e.g., 80% porosity, are resorbed faster than medium porosity silicon-based material, e.g., 50% porosity, which in turn is resorbed faster than bulk silicon-based material, which shows little to no sign of bioerosion or resorption in biological systems. Furthermore, it is understood that the average pore size of the carrier material will affect the rate of resorption. By adjusting the average pore size of a carrier material as well as the porosity of the material, the rate of bioerosion may be tuned and selected.

Silicon-based carrier materials are often prepared using high temperatures and organic solvents or acidic media to form the porous material and load the therapeutic agent within the pores. These conditions may be suitable for certain molecules such as salts, elements, and certain highly stable small organic molecules. However, for loading large organic molecules such as proteins or antibodies, caustic and/or severe conditions during the preparation or loading of the template could lead to denaturing and deactivation, if not complete degradation of the active agent. Loading large molecules such as antibodies into the carrier material under mild conditions is a feature of the methods described herein that is particularly advantageous for large organic molecules such as proteins.

The particle size of the silicon-based carrier material may also affect the rate in which the pores of the carrier material may be loaded with the therapeutic agent. Smaller particles, e.g., particles in which the largest diameter is 20 microns or less, may load more rapidly than particles in which the largest diameter is greater than 20 microns. This is particularly apparent when the pore diameters are similar in dimensions to the molecular diameters or size of the therapeutic agents. The rapid loading of smaller particles may be attributed to the shorter average pore depth that the therapeutic agent must penetrate in smaller particles.

Definitions

As used herein the specification, "a" or "an" may mean one or more. As used herein in the claim(s), when used in conjunction with the word "comprising", the words "a" or "an" may mean one or more than one. As used herein "another" may mean at least a second or more.

The terms "antibody" and "antibodies" broadly encompass naturally occurring forms of antibodies and recombinant antibodies, such as single-chain antibodies, camelized antibodies, chimeric, and humanized antibodies and multi-specific antibodies as well as fragments and derivatives of all of the foregoing, preferably fragments and derivatives having at least an antigenic binding site. Antibody derivatives may comprise a protein or chemical moiety conjugated to the antibody. The term "antibody" is used in the broadest sense and covers fully assembled antibodies, and recombinant peptides comprising them.

"Antibody fragments" comprise a portion of an intact antibody, preferably the antigen-binding or variable region of the intact antibody. Examples of antibody fragments include Fab, Fab', F(ab')2, and Fv fragments; diabodies; linear antibodies (Zapata et al. (1995) Protein Eng. 8(10): 1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

Bioerode or bioerosion, as used herein, refers to the gradual disintegration or breakdown of a structure or enclosure over a period of time in a biological system, e.g., by one or more physical or chemical degradative processes, for example, enzymatic action, hydrolysis, ion exchange, or dissolution by solubilization, emulsion formation, or micelle formation.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

Resorption or resorbing as used herein refers to the erosion of a material when introduced into or onto a physiological organ, tissue, or fluid of a living human or animal.

A "therapeutically effective amount" of a compound with respect to the subject method of treatment refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting the symptoms, clinical signs, and underlying pathology of a condition in manner to improve or stabilize a subject's condition.

Unless otherwise indicated, the term large therapeutic molecule refers to molecules with molecular weights equal to or greater than 2000 amu, or even greater than 3000 amu.

Unless otherwise indicated, the term "small molecule" refers to an organic molecule having a molecular weight less than about 2000 amu, preferably less than about 1500 amu, more preferably less than about 1000 amu, or most preferably less than about 750 amu. Preferably, a small molecule contains one or more heteroatoms.

Unless otherwise indicated, the term "sugar" refers to monosaccharides, disaccharides, oligosaccharides or sugar alcohols. Examples for the term "sugar" are, but not limited to, sucrose, fructose, glucose, erythritol, maltitol, lactitol, sorbitol, mannitol, xylitol, D-tagatose, trehalose, trehalose dehydrate, galactose, glycerol, rhamnose, cyclodextrin, raffinose, ribulose, ribose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, glucosamine, mannosamine, fucose, glucuronic acid, gluconic acid, gluconolactone, abequose, galactosamine, xylo-oligosaccharides, gentio-oligoscaccharides, galacto-oligosaccharides, sorbose, nigero-oligosaccharides, fructooligosaccharides, maltotetraol, maltotriol, maltodextrin, malto-oligosaccharides, lactulose, melibiose, or any combinations thereof.

Silicon-Based Carrier Materials

The devices and methods described herein provide, among other things, compositions comprising a porous silicon-based carrier material wherein at least one therapeutic agent and an amorphous sugar are disposed in a pore of the carrier material. The described methods use such compositions for treatment or prevention of diseases, particularly chronic diseases. Furthermore, the described methods of preparing compositions provide compositions which are characterized by sustained and controlled release of therapeutic agents, particularly large molecules such as proteins or antibodies.

The composition typically comprises a silicon-based carrier material such as elemental silicon, silicon dioxide (silica), silicon monoxide, silicates (compounds containing a silicon-bearing anion, e.g., $SiF_6^{2-}$, $Si_2O_7^{6-}$, or $SiO_4^{4-}$), or any combination of such materials. In certain embodiments, the carrier material comprises a complete or partial framework of elemental silicon and that framework is substantially or fully covered by a silicon dioxide surface layer. In other embodiments, the carrier material is entirely or substantially entirely silica.

In certain embodiments, the carrier material comprises silica, such as greater than about 50% silica, greater than about 60 wt % silica, greater than about 70 wt % silica, greater than about 80 wt % silica, greater than about 90 wt % silica, greater than about 95 wt % silica, greater than 99 wt % silica, or even greater than 99.9 wt % silica. Porous silica may be purchased from suppliers such as Davisil, Salicycle, and Macherey-Nagel.

In certain embodiments, the carrier material comprises elemental silicon, greater than 60 wt % silicon, greater than 70 wt % silicon, greater than 80 wt % silicon, greater than 90 wt % silicon, or even greater than 95% silicon. Silicon may be purchased from suppliers such as Vesta Ceramics.

Purity of the silicon-based material can be quantitatively assessed using techniques such as Energy Dispersive X-ray Analysis, X-ray fluorescence, Inductively Coupled Optical Emission Spectroscopy or Glow Discharge Mass Spectroscopy.

The carrier material may comprise other components such as metals, salts, minerals or polymers. The carrier material may have a coating (such as a polymer coating) disposed on at least a portion of the surface, e.g., to improve biocompatibility of the carrier material and/or affect release kinetics.

The silicon-based carrier material may comprise elemental silicon or compounds thereof, e.g., silicon dioxide or silicates, in an amorphous form. In some embodiments, the silicon-based carrier material comprises fumed silica. In certain embodiments, the elemental silicon or compounds thereof is present in a crystalline form. In other embodiments, the carrier material comprises amorphous silica and/or amorphous silicon. In certain embodiments, the silicon-based material is greater than about 60 wt % amorphous, greater than about 70 wt % amorphous, greater than about 80 wt % amorphous, greater than about 90 wt % amorphous, greater than about 92 wt % amorphous, greater than about 95 wt % amorphous, greater than about 99 wt % amorphous, or even greater than 99.9 wt % amorphous.

X-ray diffraction analysis can be used to identify crystalline phases of silicon-based material. Powder diffraction can be taken, for example, on a Scintag PAD-X diffractometer, e.g., equipped with a liquid nitrogen cooled germanium solid state detector using Cu K-alpha radiation.

The silicon-based material may have a porosity of about 40% to about 95% such as about 60% to about 80%. Porosity, as used herein, is a measure of the void spaces in a material, and is a fraction of the volume of voids over the total volume of the material. In certain embodiments, the carrier material has a porosity of at least about 10%, at least about 20%, at least about 30%, at least about 40%, at least about 50%, at least about 60%, at least about 70%, at least about 80%, or even at least about 90%. In particular embodiments, the porosity is greater than about 40%, such as greater than about 50%, greater than about 60%, or even greater than about 70%.

The carrier material of the compositions may have a surface area to weight ratio selected from about 20 m$^2$/g to about 2000 m$^2$/g, such as from about 20 m$^2$/g to about 1000 m$^2$/g, or even from about 100 m$^2$/g to about 300 m$^2$/g. In certain embodiments, the surface area is greater than about 200 m$^2$/g, greater than about 250 m$^2$/g or greater than about 300 m$^2$/g.

In certain embodiments, the therapeutic agent is distributed to a pore depth from the surface of the carrier material of at least about 10 microns, at least about 20 microns, at least about 30 microns, at least about 40 microns, at least about 50 microns, at least about 60 microns, at least about 70 microns, at least about 80 microns, at least about 90 microns, at least about 100 microns, at least about 110 microns, at least about 120 microns, at least about 130 microns, at least about 140 microns or at least about 150 microns. In certain embodiments, the therapeutic agent is distributed in the pores of the carrier material substantially uniformly.

The therapeutic agent may be loaded into the carrier material to a depth which is measured as a ratio to the total width of the carrier material. In certain embodiments, the therapeutic agent is distributed to a depth of at least about 10% into the carrier material, to at least about 20% into the carrier material, at least about 30% into the carrier material, at least about 40% into the carrier material, at least about 50% into the carrier material, or at least about 60% into the carrier material.

The amorphous sugar may be loaded into the carrier material to a depth which is measured as a ratio to the total width of the carrier material. In certain embodiments, the amorphous sugar is distributed to a depth of at least about 1% to at least about 9%, to at least 10% into the carrier material, to at least about 20% into the carrier material, at least about 30% into the carrier material, at least about 40% into the carrier material, at least about 50% into the carrier material, or at least about 60% into the carrier material. In some embodiments, the amorphous sugar may seal the pores.

The amorphous sugar may be loaded into the carrier material to a weight that is measured as a ratio to the combined weight of the carrier material and therapeutic agent. In certain embodiments, the amorphous sugar is loaded to a weight at least about 1% to at least about 80%, at least about 1% to at least about 70%, at least about 1% to at least about 60%, at least about 1% to at least about 50%, at least about 1% to at least about 40%, at least about 1% to at least about 30%, at least about 1% to at least about 20%, to at least about 1% to at least about 15%, about 1% to at least about 10%, about 1% to at least about 5%, about 1% to at least about 4%, at least about 1% to at least about 3%, or at least about 1% to at least about 2%. In certain embodiments, the amorphous sugar is loaded to a weight at least about 5% to at least about 10%, at least about 10% to at least about 20%, at least about 10% to at least about 30%, at least about 30% to at least about 40%, at least about 40% to at least about 50%, at least about 50% to at least about 60%, at least about 60% to at least about 70%, or at least about 70% to at least about 80%. In certain embodiments, the amorphous sugar may be loaded to a weight of about 30%. Quantification of gross loading may be achieved by a number of analytic methods, for example, gravimetric, EDX (energy-dispersive analysis by x-rays), Fourier transform infra-red (FTIR) or Raman spectroscopy of the pharmaceutical composition or by UV spectrophotometry, titrimetric analysis, HPLC or mass spectroscopy of the eluted therapeutic agent in solution. Quantification of the uniformity of loading may be obtained by compositional techniques that are capable of spatial resolution such as cross-sectional EDX, Auger depth profiling, micro-Raman and micro-FTIR.

Porous silicon-based materials of the invention may be categorized by the average diameter of the pore size. Microporous silicon-based material has an average pore size less than 2 nm, mesoporous silicon-based material has an average pore size of between 2-50 nm and macroporous silicon-based material has a pore size of greater than 50 nm. In certain embodiments, greater than 50% of the pores of the silicon-based material have a pore size from 2-50 nm, greater than 60% of the pores of the silicon-based material have a pore size from 2-50 nm, greater than 70% of the pores of the silicon-based material have a pore size from 2-50 nm, greater than 80% of the pores of the silicon-based material have a pore size from 2-50 nm, or even greater than 90% of the pores of the silicon-based material have a pore size from 2-50 nm.

In certain embodiments, the carrier material comprises porous silicon dioxide, such as mesoporous silicon dioxide. In certain embodiments, the average pore size of the carrier material is selected from 2-50 nm, such as from about 15 to about 40 nm, such as about 20 to about 30 nm. In certain embodiments, the average pore size is selected from about 2 to about 15 nm, such as about 5 to about 10 nm. In certain embodiments, the average pore size is about 30 nm.

The pore size may be preselected to the dimensional characteristics of the therapeutic agent to control the release rate of the therapeutic agent in a biological system. Typically, pore sizes that are too small preclude loading of the therapeutic agent, while oversized pores do not interact with the therapeutic agent sufficiently strongly to control the rate of release. For example, the average pore diameter for a carrier material may be selected from larger pores, e.g., 15 nm to 40 nm, for high molecular weight molecules, e.g., 200,000-500,000 amu, and smaller pores, e.g., 2 nm to 10 nm, for molecules of a lower molecular weight, e.g., 10,000-50,0000 amu. For instance, average pore sizes of about 6 nm in diameter may be suitable for molecules of molecular weight around 14,000 to 15,000 amu such as about 14,700 amu. Average pore sizes of about 10 nm in diameter may be selected for molecules of molecular weight around 45,000 to 50,000 amu such as about 48,000 amu. Average pore sizes of about 25-30 nm in diameter may be selected for molecules of molecular weight around 150,000 nm.

The pore size may be preselected to be adapted to the molecular radii of the therapeutic agent to control the release rate of the therapeutic agent in a biological system. For instance, average pore sizes of about 25 nm to about 40 nm in diameter may be suitable for molecules with a largest molecular radius from about 6 nm to about 8 nm. Molecular radii may be calculated by any suitable method such as by using the physical dimensions of the molecule based on the X-ray crystallography data or using the hydrodynamic radius which represents the solution state size of the molecule. As the solution state calculation is dependant upon the nature of the solution in which the calculation is made, it may be preferable for some measurements to use the physical dimensions of the molecule based on the X-ray crystallography data. As used herein the largest molecular radius reflects half of the largest dimension of the therapeutic agent.

In certain embodiments, the average pore diameter is selected to limit the aggregation of molecules, e.g., proteins, within a pore. It would be advantageous to prevent biomolecules such as proteins from aggregating in a carrier material as this is believed to impede the controlled release of molecules into a biological system. Therefore, a pore that, due to the relationship between its size and the size of a biomolecule, allows, for example, only one biomolecule to enter the pore at any one time, will be preferable to a pore that allows multiple biomolecules to enter the pore together and aggregate within the pore. In certain embodiments, multiple biomolecules may be loaded into a pore, but due to the depth of the pore, the proteins distributed throughout this depth of the pore will aggregate to a lesser extent.

In certain embodiments, the therapeutic agent is selected from any agent useful in the treatment or prevention of diseases. In certain embodiments, the agent is selected from small molecule therapeutic agents, i.e., compounds with molecular weights less than 1000 amu. In preferred embodiments, the therapeutic agents are selected from large molecules with molecular weight equal to or greater than 1000 amu. In certain embodiments, the therapeutic agent of the invention is a biomolecule. Biomolecules, as used herein, refer to any molecule that is produced by a living organism, including large polymeric molecules such as proteins, polysaccharides, and nucleic acids as well as small molecules such as primary metabolites, secondary metabolites, and natural products or synthetic variations thereof. In particular, proteins such as antibodies, ligands, and enzymes may be used as therapeutic agents of the invention. In particular embodiments, the biomolecules of the invention have molecular weights ranging from about 10,000 amu to about 500,000 amu. In certain embodiments, the therapeutic agent is selected from one or more monoclonal antibodies, such as ranibizumab (Lucentis) and bevacizumab (Avastin).

In certain embodiments, the therapeutic agent has a molecular weight between 10,000 and 50,000 amu, between 50,000 and 100,000 amu or between 100,000 and 150,000 amu. In certain embodiments, the therapeutic agent is a protein with a molecular weight between 5,000 amu and 200,000 amu, such as about 10,000 to about 150,000 amu.

The size of a therapeutic agent may alternatively be characterized by the molecular radius, which may be determined, for example, through X-ray crystallographic analysis or by hydrodynamic radius. The therapeutic agent may be a protein, e.g., with a molecular radius selected from 0.5 nm to 20 nm such as about 0.5 nm to 10 nm, even from about 1 to 8 nm.

A therapeutic agent with molecular radius from 1 to 2.5 nm may be advantageously used with a carrier material with a minimum pore radius of from 4.5 to 5.8 nm. A therapeutic agent with a molecular radius of 7 nm may be advantageously used with a carrier material with a minimum pore radius of from 11 to 13 nm, such as about 12 nm. For example, insulin with a hydrodynamic radius of 1.3 nm may be used with a carrier material that has an average minimum pore radius of 4.8 nm.

The protein-pore differential may be used to choose a suitable carrier material to accommodate the therapeutic agent. This calculation subtracts the molecular radius from the pore radius. Typically, the radius of the therapeutic agent would be the hydrodynamic radius or largest radius determined through x-ray crystallographic analysis. The pore radius would typically be the average pore radius of the carrier material. For example, the pore-protein differential for insulin, with a hydrodynamic radius of 1.3 nm and a pore with a minimum radius of 4.8 nm has a protein-pore differential of 3.5 nm. In certain embodiments, the protein-pore differential is selected from 3 to 6 nm, such as from 3.2 to 4.5 nm. The protein-pore differential may be about 3.2 nm, about 3.3 nm, about 3.4 nm, about 3.5 nm, about 3.6 nm, about 3.7 nm, about 3.8 nm, about 3.9 nm, about 4.0 nm, about 4.1 nm, about 4.2 nm, about 4.3 nm, about 4.4 nm or about 4.5 nm.

In certain embodiments, the therapeutic agent is an antibody and the average pore size of the carrier material is selected from about 20 nm to about 40 nm such as from about 25 nm to 35 nm such as about 30 nm. In certain embodiments, the therapeutic agent is an antibody selected from bevacizumab or ranibizumab and the average pore size of the carrier material is selected from about 20 nm to about 40 nm such as from about 25 nm to 35 nm such as about 30 nm. In certain embodiments, the therapeutic agent is bevacizumab and the average pore size of the carrier material is about 30 nm.

In certain embodiments, the walls of the carrier material that separate the pores have an average width of less than 5 nm, such as about 4.8 nm, about 4.6 nm, about 4.4 nm, about 4.2 nm, about 4.0 nm, about 3.8 nm, about 3.6 nm, about 3.4 nm, about 3.2 nm, about 3.0 nm, about 2.8 nm, or even about 2.6 nm. In certain embodiments, the walls of the carrier material that separate the pores have an average width of less than about 3 nm, such as about 2.8 nm, about 2.6 nm, about 2.4 nm, about 2.2 nm, about 2.0 nm, about 1.8 nm, about 1.6 nm, about 1.4 nm, about 1.2 nm, about 1.0 nm, or even about 0.8 nm.

Dimensionality and morphology of the carrier material can be measured, for example, by Transmission Electron Microscopy (TEM) using a 2000 JEOL electron microscope operating, for example, at 200 keV. Samples for TEM can be prepared by dispensing a large number of porous carrier material particles onto a holey carbon film on a metal grid, via a dilute slurry.

In certain embodiments, the pores of the carrier material define space having a volume of about 0.1 mL/g to about 5 mL/g of the carrier material. In certain embodiments, the pore volume is about 0.2 mL/g to about 3 mL/g, such as about 0.4 mL/g to about 2.5 mL/g, such as about 1.0 mL/g to about 2.5 mL/g.

In certain embodiments, the load level of the carrier material is up to 80% by weight based on the combined weight of the carrier material and the therapeutic agent. The load level is calculated by dividing the weight of the loaded therapeutic agent by the combined weight of the loaded therapeutic agent and carrier material and multiplying by 100. In certain embodiments, the load level of the carrier material is greater than 1%, such as greater than 3%, such as greater than 5%, such as greater than 10%, such as greater than 15%, greater than 20%, greater than 25%, greater than 30%, greater than 35%, greater than 40%, greater than 45%, such as greater than 50%, such as greater than 60%, or greater than 70%. The load level may be between about 5% and about 10%. In certain embodiments, the load level of the carrier material is between about 10% and about 20%, between about 20% and about 30%, between about 30% and about 40%, between about 40% and about 50%, between about 50% and about 60%, between about 60% and about 70% or between about 70% and about 80% by weight.

In certain embodiments, the load level of the carrier material is up to 40% weight based on the weight of the composition. In certain embodiments, the load level of the carrier material is greater than 1%, such as greater than 3%, such as greater than 5%, such as greater than 10%, such as greater than 15%, greater than 20%, greater than 25%, greater than 30%, or greater than 35%. The load level may be between about 5% and about 10%. In certain embodiments, the load level of the carrier material is between about 10% and about 20%, between about 20% and about 30%, between about 30% and about 40% by weight. The load level is calculated by dividing the weight of the loaded therapeutic agent divided by the weight of the composition and multiplying by 100. The composition may comprise the carrier material, the therapeutic agent, the amorphous sugar and optionally other components such as a crystallization inhibitor. In some embodiments, the composition comprises:
a therapeutic agent (such as a protein) in the range of 1% to 40% by weight,
an amorphous sugar in the range of 1% to 50% by weight, and
a carrier material in the range of 10% to 30% by weight.

The load volume of the carrier materials described herein may be evaluated in terms of the volume of the pores in the porous material being occupied by the therapeutic agent. The percentage of the maximum loading capacity that is occupied by the therapeutic agent (that is, the percentage of the total volume of the pores in the porous carrier material that is occupied by the therapeutic agent) for carrier materials according to the invention may be from about 30% to about 100%, such as from about 50% to about 90%. For any given carrier material, this value may be determined by dividing the volume of the therapeutic agent taken up during loading by the void volume of the carrier material prior to loading and multiplied by one hundred.

In certain embodiments, the carrier materials of the invention are particles that, measured at the largest diameter, have an average size of about 1 to about 500 microns, such as about 5 to about 100 microns. In certain embodiments, a single carrier material particle measured at its largest diameter is about 1 to about 500 microns, such as about 5 to about 500 microns.

In order to increase the rate of loading of the particles of the invention, it may be advantageous to use relatively small particles. As smaller particles have pores with less depth for the therapeutic agent to penetrate, the amount of time needed to load the particles may be reduced. This may be particularly advantageous when the pore diameters are similar in dimensions to the molecular diameters or size of the therapeutic agents. Smaller particles may be from 1-20 microns, such as about 10-20 microns, e.g., about 15-20 microns, measured at the largest dimension.

In some aspects, greater than 60%, greater than 70%, greater than 80% or greater than 90% of the particles have a particle size of from 1-20 microns, preferably 5-15 microns, measured at the largest dimension. The particles may have an average particle size between 1 and 20 microns such as between 5-15 microns or about 15 microns, about 16 microns, about 17 microns, about 18 microns, about 19 microns.

Particle size distribution, including the mean particle diameter can be measured, for example, using a Malvern Particle Size Analyzer, Model Mastersizer, from Malvern Instruments, UK. A helium-neon gas laser beam may be projected through an optical cell containing a suspension of the carrier material. Light rays striking the carrier material are scattered through angles which are inversely proportional to the particle size. The photodetector array measures the light intensity at several predetermined angles and electrical signals proportional to the measured light flux values are then processed by a microcomputer system against a scatter pattern predicted from the refractive indices of the sample carrier material and aqueous dispersant.

Larger carrier material particles or implants are also envisioned for controlled delivery of therapeutic agents. The particles/implants of the invention may have an average size of about 1 mm to about 5 cm measured at the largest dimension. In certain embodiments, the particles/implants have an average size of about 5 mm to about 3 cm measured at the largest dimension. Particles greater than 1 mm, as measured at the largest dimension, may be useful for intramuscular subcutaneous, intravitreal or subdermal drug delivery.

In certain embodiments, the amorphous sugars described herein present in the pores are used to stabilize sensitive therapeutic compounds, such as biomolecules, e.g., antibodies. In certain embodiments, biomolecules that are partially or wholly unstable at elevated temperatures, such as room temperature or above, can be made stable at room temperature for prolonged periods of time. For example, the biomolecule formulated with amorphous sugars within the carrier material is stable to drying under reduced pressure at room temperature.

In certain embodiments, the porous carrier materials described herein are used to stabilize sensitive therapeutic compounds, such as biomolecules, e.g., antibodies. In certain embodiments, biomolecules that are partially or wholly unstable at elevated temperatures, such as room temperature or above, can be made stable at room temperature for prolonged periods of time. The biomolecules may be loaded into a carrier material such that an aqueous suspension of the biomolecule loaded into the carrier material is more stable than a corresponding aqueous solution of the biomolecule (i.e., an identical aqueous solution with and without the addition of the porous carrier material). For example, the biomolecule within the carrier material may have a half-life at room temperature (e.g., about 23° C.) that is greater than a half-life of the biomolecule without the carrier material under the same conditions. In certain embodiments, a biomolecule in the pores of the carrier material has a half-life that is at least twice as long as the biomolecule outside of the carrier material under the same conditions, more preferably, at least five times, at least 10 times, at least than 15 times, at least 20 times, at least 30 times, at least 40 times, at least 50 times, at least 60 times, or at least 100 times as long as the biomolecule outside of the carrier material. For example, an antibody within the pores of the carrier material may have a half-life that is at least 10 times as long as the antibody outside of the carrier material, more preferably, at least 20 times as long.

Similarly, biomolecules formulated with amorphous sugars may have a longer shelf life within the pores of the carrier material than in a corresponding aqueous solution, preferably at least twice as long, at least five times as long, at least 10 times as long, at least 20 times as long, at least 30 times as long, at least 40 times as long, at least 50 times as long, at least 60 times as long or at least 100 times as long. For example, an antibody within the pores of the carrier material may have a longer shelf life than an antibody outside of the carrier material, preferably at 10 times as long, at least 20 times as long.

In certain embodiments, porous compositions comprising the carrier material and, a biomolecule, such as an antibody, and amorphous sugars exhibit stability at the temperature of 25° C. for at least 15 days, or even about 1 month. Additionally or alternatively, in certain embodiments, the antibody-loaded carrier materials are stable at 25° C. for at least 6 months, at least 1 year, at least 1.5 years, at least 2 years, at least 2.5 years, at least 3 years or at least 4 years. Stability may be assessed, for example, by high performance size exclusion chromatography (HPSEC) or by comparing the biological activity of the stored biomolecule-loaded compositions against a sample of freshly prepared biomolecule-loaded compositions or against the activity of the compositions as measured prior to storage. Activity of antibodies, for example, can be assessed by various immunological assays including, for example, enzyme-linked immunosorbent assay (ELISA) and radioimmunoassay. Preferably, at the end of the storage period, the activity of the stored compositions is at least 75%, at least 80%, at least 85%, at least 90%, at least 95%, at least 98%, at least 99%, at least 99.5%, at least 99.8%, or even at least 99.9% of the activity of the corresponding freshly prepared compositions. Accordingly, the invention contemplates methods of treatment wherein biomolecule-loaded compositions are stored at 25° C. for at least 6 months, at least 1 year, at least 1.5 years, at least 2 years, at least 2.5 years, at least 3 years or at least 4 years prior to administering the compositions to a patient.

The invention further comprises methods of stabilizing biomolecules. Methods of the invention comprise loading biomolecules into the pores of the carrier material through any suitable method to form the compositions of the invention.

Methods of Preparation

The invention also provides methods of preparing silicon-based carrier materials. In certain embodiments, porous silicon-based carrier material may be prepared synthetically. For example, porous silica may be synthesized by reacting tetraethyl orthosilicate with a template made of micellar rods. In certain embodiments, the result is a collection of spheres or rods that are filled with a regular arrangement of pores. The template can then be removed, for example, by washing with a solvent adjusted to the proper pH. In certain embodiments, the porous silicon-based carrier material may be prepared using a sol-gel method or a spray drying method. In certain embodiments, the porous silicon based carrier material may be prepared by flame hydrolysis of silicon tetrachloride in an oxy-hydrogen flame. In certain embodiments, the preparation of the carrier material involves one or more techniques suitable for preparing porous silicon-based material.

Pores may be introduced to the silicon-based carrier material through techniques such as anodization, stain etching, or electrochemical etching. In an exemplary embodiment, anodization employs a platinum cathode and silicon wafer anode immersed in Hydrogen Fluoride (HF) electrolyte. Corrosion of the anode producing pores in the material is produced by running electrical current through the cell. In particular embodiments, the running of constant DC is usually implemented to ensure steady tip-concentration of HF resulting in a more homogeneous porosity layer.

In certain embodiments, pores are introduced to the silicon-based carrier material through stain-etching with hydrofluoric acid, nitric acid and water. In certain embodiments, a combination of one or more stain-etching reagents are used, such as hydrofluoric acid and nitric acid. In certain embodiments, a solution of hydrofluoric acid and nitric acid are used to form pores in the silicon-based material.

The porosity of the material can be determined by weight measurement. BET analysis may be used to determine any one or more of the pore volume, pore size, pore size distribution and surface area of the carrier material. BET theory, named after the combined surname initials of authors of the theory, applies to the physical adsorption of gas molecules on a solid surface and serves as the basis for an important analysis technique for the measurement of the specific surface area of a material (J. Am. Chem. Soc. v. 60, p 309 (1938)). The BET analysis may be performed, for example, with a Micromeritics ASAP 2000 instrument available from Micromeritics Instrument Corporation, Norcross, Ga. In an exemplary procedure, the sample of carrier material may be outgassed under vacuum at temperatures, for example, greater than 200° C. for a period of time such as about 2 hours or more before the measurements are taken. In certain embodiments, the pore size distribution curve is derived from the analysis of the adsorption branch of the isotherm output. The pore volume may be collected at the $P/P0=0.985$ single point.

One or more drying techniques may be used in the preparation of porous silicon-based materials of the invention. For example, to prevent cracking of the porous silicon-based material, the material may be dried by supercritical drying, freeze drying, pentane drying, slow evaporation, spray drying or vacuum-assisted flash drying. Supercritical drying involves superheating the liquid pore above the critical point to avoid interfacial tension. Freeze drying involves freezing and subliming any solvents under vacuum. Pentane drying uses pentane as the drying liquid instead of water and as a result may reduce capillary stress due to the lower surface tension. Slow evaporating is a technique which can be implemented following the water or ethanol rinsing and may be effective at decreasing the trap density of solvent within the material. Spray drying is a technique whereby a solution of protein and sugar is spray dried so that the water is evaporated sufficiently quickly to allow the sugar to go from a solution to a solid without reordering into a crystal. Vacuum-assisted flash drying is a technique whereby the porous matrix assists the rapid drying of the formulation under reduced pressure whilst stabilising the amorphous sugar. Vacuum-assisted flash drying may be performed at room temperature, which is desirable for physically stabilized amorphous systems such as biomolecules and sugars.

The surface of the porous silicon-based material may be modified to exhibit properties such as improved stability, cell adhesion or biocompatibility. Optionally, the material may be exposed to oxidizing conditions such as through thermal oxidation. In an exemplary embodiment, the process of thermal oxidation involves heating the silicon-based material to a temperature above 1000° C. to promote full oxidation of the silicon-based material. Alternatively, the surface of the carrier material may be oxidized so that the carrier material comprises a framework of elemental silicon partially, substantially or fully covered by an oxidized surface such as a silicon dioxide surface.

The surface of the porous silicon-based material or a portion thereof may be derivatized. In an exemplary embodiment, the surface of a porous silicon-based material may be derivatized with organic groups such as alkanes or alkenes. In a particular embodiment, the surface of the carrier material may be derivatized by hydrosilation of silicon. In particular embodiments, the derivatized carrier materials may function as biomaterials, incorporating into living tissue.

Any one or more of electrostatic interactions, capillary action and hydrophobic interactions may enable loading of the therapeutic agent into the pores of the carrier material. In certain embodiments, the carrier material and therapeutic molecules are placed in a solution and the large molecules, e.g., proteins or other antibodies, are drawn from the solution into the pores of the carrier material, reminiscent of a molecular sieve's ability to draw water from an organic liquid. Hydrophobic drugs may be better suited for loading into carrier materials that are predominantly formed from silicon (e.g., greater than 50% of the material is silicon) while hydrophilic drugs may be better suited for loading into a carrier material that is characterized as mostly silica (e.g., greater than 50% of the carrier material is silica). In certain embodiments, the loading of large molecules into the pores of the carrier material is driven by external factors such as sonication or heat. The carrier material may have an electrostatic charge and/or the therapeutic agent may have an electrostatic charge. Preferably, the carrier material has the opposite electrostatic charge as the therapeutic agent such that adsorption of the therapeutic agent into the pores of the carrier material is facilitated by the attractive electrostatic forces. In certain embodiments, the therapeutic agent or the carrier material itself does not have an electrostatic charge under neutral conditions, but is polarizable or ionizable. For example, in such embodiments, the carrier material and/or the therapeutic agent may be ionized to facilitate the adsorption of the therapeutic agent in the pores of the carrier material. For example, in the body, at physiological pH, silicon dioxide exhibits a negatively charged surface, which promotes electrostatic adsorption of positively charged peptides. Similarly, molecules with carboxylic acids, phosphoric, and/or sulfonic acids are ionized with increasing pH to negatively charged carboxylate, phosphate, and/or sulfonate salts, while nitrogenated molecules (e.g., bearing amine, guanidine, or other basic substituents) are protonated with decreasing pH to ammonium, guanidinium, or other positively charged salts.

The carrier material may comprise a coating or surface modification to attract the therapeutic agent into the pores. In certain embodiments, the carrier material is coated or modified in whole or in part with a material comprising moieties that are charged in order to attract a protein or antibody into the pores of the carrier material. In other embodiments, the moieties may be appended directly to the carrier material. For example, amine groups may be covalently appended onto the surface of the carrier material such that when protonated at physiological pH, the surface of the carrier material carries a positive charge, thereby, for example, attracting a protein or antibody with a negatively charged surface. In other embodiments, the carrier material may be modified with carboxylic acid moieties such that when deprotonated at physiological pH, the carrier material carries a negative charge, thereby attracting proteins or antibodies with positively charged surfaces into the pores.

In certain embodiments, the therapeutic agent may be incorporated into the carrier material following complete formation of the carrier material. Alternatively, the therapeutic agent may be incorporated into the carrier material at one or more stages of preparation of the carrier material. For example, the therapeutic agent may be introduced to the carrier material prior to a drying stage of the carrier material, or after the drying of the carrier material or at both stages. In certain embodiments, the therapeutic agent may be introduced to the carrier material following a thermal oxidation step of the carrier material.

More than one therapeutic agent may be incorporated into a carrier material. In certain such embodiments, each therapeutic agent may be individually selected from small organic molecules and large molecules such as proteins and antibodies. For example, an ocular carrier material may be impregnated with two therapeutic agents for the treatment of glaucoma, or one therapeutic agent for the treatment of macular degeneration and another agent for the treatment of glaucoma.

In certain aspects, e.g., when both small molecule therapeutic agents and larger molecular therapeutic agents such as proteins are incorporated into a carrier material, the therapeutic agents may be incorporated into the carrier material at different stages of the preparation of the composition. For example, a small molecule therapy may be introduced into the carrier material prior to an oxidation or drying step and a large molecule therapeutic agent may be incorporated following an oxidation or drying step. Similarly, multiple different therapeutic agents of the same or different types may be introduced into a finished carrier material in different orders or essentially simultaneously.

When a carrier material comprises a single material, or combination of multiple materials with multiple pore sizes, the larger therapeutic agent is preferably added to the carrier material prior to adding the smaller therapeutic agent to avoid filling the larger pores with the smaller therapeutic agent and interfering with adsorption of the larger therapeutic agent. For example, if a carrier material comprises a single material, or combination of multiple materials, that has some well-defined pores that are about 6 nm in diameter (i.e., suitable for molecules of molecular weight around 14,000 to 15,000 amu) and some well-defined pores that are about 10 nm in diameter (i.e., suitable for molecules of molecular weight around 45,000 to 50,000 amu), the latter therapeutic agent (i.e., the one with molecules of molecular weight around 45,000 to 50,000 amu) are preferably added to the carrier material prior to adding the smaller therapeutic agent (i.e., the one with molecules of molecular weight around 14,000 to 15,000 amu). Alternatively and additionally, in the embodiment wherein the two different porous materials together comprise the device, each carrier material may be separately loaded with a different therapeutic agent and then the carrier materials may be combined to yield the device.

The therapeutic agent may be introduced into the carrier material in admixture or solution with one or more pharmaceutically acceptable excipients. The therapeutic agent may be formulated for administration in any suitable manner, typically in the form of a composition, suitably for subcutaneous, intramuscular, intraperitoneal or epidermal introduction or for implantation into an organ (such as the liver, lung or kidney). Therapeutic agents according to the invention may be formulated for parenteral administration in the form of an injection, e.g., intraocularly, intravenously, intravascularly, subcutaneously, intramuscularly or infusion, or for oral administration.

The carrier material may be in any suitable form prior to loading with the therapeutic agent such as in the form of a dry powder or particulate or formulated in an aqueous slurry, e.g., with a buffer solution or other pharmaceutically acceptable liquid. The therapeutic agent may be in any suitable form prior to loading into the carrier material such as in a solution, slurry, or solid such as a lyophilisate. The carrier material and/or the therapeutic agent may be formulated with other components such as excipients, preservatives, stabilizers, e.g., sugars, or therapeutic agents, e.g., antibiotic agents.

The therapeutic agent may be formulated (and packaged and/or distributed) as a solution with a concentration of >50 mg/mL, such as >60 mg/mL, such as >75 mg/mL. In an exemplary embodiment, the therapeutic agent is becacizumab and the becacizumab may be formulated with a concentration of >50 mg/mL, such as >60 mg/mL, such as >75 mg/mL in, for example, a phosphate buffer solution. The therapeutic agent may be formulated (and packaged and/or distributed) with a surfactant and/or a stabilizer, e.g., sugars, wherein the therapeutic agent has a maximum concentration of 50 mg/mL. A protein fragment, such as an antibody fragment, may be formulated (and packaged and/or distributed) as a solution with a concentration of >10 mg/mL, >15 mg/mL or >20 mg/mL.

The therapeutic agent may be formulated (and packaged and/or distributed) with stabilizers, excipients, surfactants or preservatives. In some embodiments, the stabilizers, excipients, surfactants or preservatives are sugars. In particular embodiments, the sugars are selected from thehalose, sucrose, mannitol, sorbitol, xylitol or glycerol. In other embodiments, the therapeutic agent is formulated (and packaged and/or distributed) essentially free of any one or more of stabilizers, excipients, surfactants and preservatives, e.g., contains less than 1 mg/mL or preferably less than 0.1 mg/mL of a stabilizer, excipients, surfactant or preservative. The formulation of the therapeutic agent may contain less than 1 mg/mL of surfactants such as less than 0.1 mg/mL of surfactants.

In certain embodiments, the composition may comprise a coating surrounding the particles (e.g., the carrier material/agent/sugar complex) to regulate release of the therapeutic agent. For example, the particles may be coated with a polymeric coating (e.g., by spray-drying) an excipient such as cocoa butter to obtain a desired release profile of the therapeutic agent from the delivery vehicle. A polymeric coating may be biodegradable or non-biodegradable, permeable or non-permeable to release of the agent. One of skill in the art will recognize that it is preferred for the polymer to be permeable, biodegradable, or both in order for the agent to be released from the particles.

In certain embodiments, the particles of the composition may be coated with a range of polymers/solvents such as polyurethane, polysilicone, poly(ethylene-co-vinyl acetate), polyvinyl alcohol, polyanhydride, polylactic acid (PLA), poly(lactic-co-glycolic acid) (PLGA), polyorthoester, polyalkylcyanoacrylate, polycaprolactone, derivatized cellulose based polymers and derivatives and copolymers thereof, such as polymethacrylate-based copolymers, to obtain a desired release profile of the therapeutic agent from the carrier material.

Methods of Use

In certain embodiments, the compositions are used to prevent or treat a condition of a patient. The various embodiments provided herein are generally provided to deliver a therapeutically affective amount of a therapeutic agent locally, i.e., to the site of the pain, disease, etc., in a patient. In certain embodiments, the compositions of the invention may be delivered to any site on the surface or within the body of a patient. For example, compositions of the invention may used on the surface of the skin or eye or may be implanted under the skin, within a muscle, within an organ, adjacent to a bone, within the eye or at any other location where controlled release of a therapeutic agent would be beneficial. The compositions may be administered intravitreally, subcutaneously, subconjunctivally, intraperitoneally, intramuscularly or subretinally. In certain embodiments, the compositions of the invention is delivered to the surface of the eye or within the eye such as within the sclera of the eye or within the vitreous of the eye.

In certain embodiments, the compositions of the invention are used to treat intraocular diseases, such as back of the eye diseases. Exemplary intraocular diseases include glaucoma, age-related macular degeneration such as wet age-related macular degeneration, diabetic macular edema, geographic atrophy, choroidal neovascularization, uveitis, diabetic retinopathy, retinovascular disease and other types of retinal degenerations.

In certain embodiments, the compositions of the invention are used to treat diseases on the surface of the eye. Exemplary diseases include viral keratitis and chronic allergic conjunctivitis.

In certain embodiments, the method for treating an ocular condition comprises disposing the composition on the surface of the eye or within the eye such as within the vitreous or aqueous of the eye. In certain embodiments, the composition is injected or surgically inserted within the eye of the patient. In certain embodiments, the composition is injected within the eye of the patient, e.g., into the vitreous of the eye. In certain embodiments, the composition is injected as a composition. In certain embodiments, a composition comprises multiple carrier material particles. The composition may comprise particles with an average size between about 1 micron to about 500 microns. In certain embodiments, the composition comprises particles with an average particle size between 5 microns and 300 microns such as between about 5 microns and 100 microns.

In certain aspects, compositions of the invention may be used to administer any therapeutic agent in a sustained fashion to a patient in need thereof. The compositions of the invention are not limited to ocular and intraocular use and may be used in any part of the body. For example, compositions of the invention may be used to administer therapeutic agents subdermally similar to the Norplant contraceptive device. In other embodiments, compositions of the invention are used to administer biomolecules over a sustained period of time for the treatment of chronic diseases such as arthritis. For example, compositions of the invention may be used to deliver therapeutic agents such as etanercept or adalimumab to patients in need of this therapy. The compositions of the invention may be located any place in the body such as within a muscle. The composition may comprise multiple small particles such as multiple particles 500 microns or less. The compositions may comprise larger particles such as greater than 500 microns or one or more particles greater than 1 mm in size such as greater than 10 mm.

The therapeutic agent may be a small molecule or biomolecule. The therapeutic agent may be released to the patient over the course of up to four, six, or even up to twelve months after administration. In some embodiments, the therapeutic agent is released to the patient over the course of 1 month to 6 months. In preferred embodiments, the therapeutic agent is released to the patient over the course of 2 days to 2 weeks. In preferred embodiments, the therapeutic agent is released to the patient over the course of 4 days to 12 days. In preferred embodiments, the therapeutic agent is released to the patient over the course of 6 days to 10 days. In preferred embodiments, the therapeutic agent is released to the patient over the course of 7 days.

In certain embodiments, the composition is injected or surgically inserted subcutaneously. In other embodiments, the composition is delivered to the patient intravenously or intraarticularly.

In some embodiments, the composition is administered orally. In some embodiments, the composition is orally administered and comprises a vaccine. Oral administration can be used, for instance, to deliver active agents to the stomach, small intestine, or large intestine. Formulations for oral administration may be in the form of capsules, cachets, pills, tablets, lozenges (using a flavored basis, usually sucrose and acacia or tragacanth), powders, granules, and the like, each containing a predetermined amount of an active ingredient. Solid dosage forms for oral administration (capsules, tablets, pills, dragees, powders, granules, and the like), may comprise the device and one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like. The oral compositions can also include sweetening, flavoring, perfuming, and preservative agents.

In certain embodiments, multiple particle populations are delivered to the patient such as two particle populations, three particle populations, four particle populations or five particle populations or more. The particle populations may be substantially identical in size or composition or may have different sizes, a make up of different carrier materials or be loaded with different therapeutic agents. The multiple particle populations may be administered to the patient simultaneously or over a period of time, and at one or more locations of the patient's body.

In certain embodiments, the therapeutic agent is released from the composition into the surrounding biological system over a duration of days, weeks, months or years. In certain such embodiments, the therapeutic agent is released over the course of time selected from one day to two years, such as from two weeks to about one year, such as about one month to about one year. The composition may release the drug into the eye over the course of 1 day to 12 months, such as 1 day to 6 months, such as over the course of 1 week to 3 months. In certain embodiments, the therapeutic agent is released within two years, such as with 18 months, within 15 months, within one year, within 6 months, within three months, or even within two months. In certain embodiments, the release of the therapeutic agent from the composition occurs in a controlled manner such that a large percentage of the total impregnated therapeutic agent is not released immediately or within a short time span, e.g., within minutes or hours of administration. For example if the desired drug delivery time is 2 months, the total impregnated therapeutic agent may, for example, be released at a rate of approximately $\frac{1}{60}$th of the impregnated therapeutic agent per day. In certain embodiments, controlled release involves the release of a therapeutic agent over the course of, for example, 1 month, 2 months, 3 months, 4 months, 5 months, 6 months, 7 months, or 8 months, wherein the amount of the agent released charts linearly with respect to the full course of delivery. In some embodiments, there may be a burst effect of the therapeutic agent shortly after administration, followed by a substantially constant release over a subsequent period of time. The burst effect may last, for example, from 1-10 days during which a percentage of the loaded drug is released. After the burst, the remainder of the therapeutic agent may be released constantly over a certain period of time. For example, in certain embodiments, less than 10% of the therapeutic agent is released over the first day following administration, and a further 50% is constantly released over the subsequent 2-30 days, e.g. at a substantially constant rate of release. In another exemplary embodiment, less than 10% of the therapeutic agent is released in the first 5 days following administration, followed by constant release of 50% of the therapeutic agent over the subsequent 25 days. By substantially constant release, it is meant that that rate of release of the therapeutic agent from the composition is essentially constant over a certain period of time.

In certain embodiments, the therapeutic agent begins being released immediately after being administered. In certain embodiments, the therapeutic agent is released over the course of approximately 3 to 8 months, such as over the course of about 6 months. In certain embodiments, additional compositions of the invention are administered to a patient at appropriate periods to ensure a substantially continuous therapeutic effect. For example, successive doses of an composition that releases a drug for a period of six months may be administered biannually, i.e., once every six months.

The release of drug from the composition and into the body can be assessed by serum and vitreous analyses, e.g., using ELISA.

In certain embodiments, the composition may completely or partially bioerode within a biological system. In certain embodiments, the composition may be resorbed by the biological system. In certain embodiments, the composition may be both bioerodible and resorbable in the biological system. In certain embodiments, the carrier material may be partially bioactive such that the material incorporates into living tissue. In some embodiments, after implantation, the carrier material does not substantially mineralize or attract mineral deposits. For instance, in some embodiments, the carrier material does not substantially calcify when placed in situ in a site where calcification is undesirable.

In certain embodiments, the composition may bioerode in a biological system. In certain embodiments, greater than about 80% of the carrier material will bioerode in a biological system, such as greater than about 85%, greater than about 90%, greater than about 92%, greater than about 95%, greater than about 96%, greater than about 97%, greater than about 98%, greater than about 99%, greater than 99.5%, or even greater than 99.9%. In certain embodiments, where the carrier material bioerodes, it is partially or completely resorbed.

In certain embodiments, the composition may substantially bioerode of the course of 1 week to 3 years. In certain embodiments, substantially bioerosion refers to erosion of greater than 95% of the carrier material. In certain embodiments, substantial bioerosion occurs of the course of about 1 month to about 2 years, such as about 3 months to 1 year. In certain embodiments, substantial bioerosion occurs within about 3 years, such as within about 2 years, within about 21 months, within about 18 months, within about 15 months, within about 1 year, within about 11 months, within about 10 months, within about 9 months, within about 8 months, within about 7 months, within about 6 months, within about 5 months, within about 4 months, within about 3 months, within about 2 months, within about 1 month within about 3 weeks, within about 2 weeks, within about 1 week, or even within about 3 days. In certain embodiments, where the carrier material bioerodes, it is partially or completely resorbed.

In certain embodiments, the extent of bioerosion may be evaluated by any suitable technique used in the art. In exemplary embodiments, the bioerosion is evaluated through an in vitro assay to identify degradation products or in vivo histology and analysis. The biodegradability kinetics of the porous carrier material may be assessed in vitro by analyzing the concentration of the principle degradation product in the relevant body fluid. For porous silicon-based carrier materials in the back of the eye, for example, the degradation product may include orthosilicic acid, quantified, for example, by the molybdate blue assay, and the body fluid may be simulated or real vitreous humor. The biodegradability kinetics in vivo may be determined by implanting a known quantity of the porous silicon-based material into the relevant body site and monitoring its persistence over time using histology combined with, for example, standard microanalytical techniques.

EXAMPLES

Materials
Specifications of Commercial Porous Silica

| Supplier | Trade Name | Nominal Pore Size (Å) | Surface Area (m²/g) | Pore Volume (mL/g) |
|---|---|---|---|---|
| Grace Davison Discovery Sciences | Davisil | 60 | 550 | 0.9 |
| | | 150 | 330 | 1.2 |
| | | 250 | 285 | 1.8 |
| | | 500 | 80 | 1.1 |
| | | 1000 | 40 | 1.1 |
| SiliCycle | SiliaSphere PC | 300 | 100 | 1.1 |

Example 1

Preparation of Sugar and Porous Silica Formulation

The co-formulations of mannitol, sorbitol or xylitol with 60 Å porous silica (such as Davisil) can be achieved through melt loading. Approximately equal weights of silica and sugar are mixed by hand in a zip-lock bag; then transferred to a suitable sample vial. The mixture is heated at the melting point of the sugar for a period of five minutes.

Example 2

Preparation of Trehalose and Porous Silica Formulation

The co-formulation of trehalose with 60 Å porous silica (such as Davisil) can be achieved through immersion loading. Approximately 1000 mg of porous silica is immersed in 5 mL of a concentrated solution of trehalose (500 mg/mL) and incubated for a period of two hours at room temperature and pressure, under continual agitation. This loading solution can be prepared using trehalose dihydrate crystals. The starting weight of these crystals must therefore be adjusted, so that the final concentration of the solution is approximately 500 mg/mL. Following incubation, the co-formulation is recovered from the loading solution via spin filtration using a PVDF filter (2 minutes at 13000 rpm), frozen to minus 20° C. and freeze-dried. To prevent re-crystallisation of the sugar during centrifugation, samples are heated to approximately 40° C. during this process. After the sugar has been loaded, the formulation is dried.

Example 3

Preparation of Sucrose and Porous Silica Formulation

The co-formulation of sucrose with 60 Å porous silica (such as Davisil) can be achieved through immersion loading. Approximately 1000 mg porous silica is immersed in 5 mL of a saturated solution of sucrose (2 g/mL) and incubated for a period of two hours at room temperature, pressure and under continual agitation. The sample is recovered via spin filtration using a PVDF filter, frozen to minus 20° C. and freeze-dried. To prevent re-crystallisation of the sugar during centrifugation, this procedure is completed at a temperature of approximately 40° C. After the sugar has been loaded, the formulation is dried.

Example 4

Preparation of Sucrose and Porous Silica Formulations

Bevacizumab (2 mL of a 1 mg/mL solution) was incubated with porous silica 250 Å (e.g., Davisil) (40 mg) for 18 hours at room temperature. Sucrose (2 g) was added and the composition was incubated for 20 hours. After incubation the material was recovered via centrifugation through a 0.45 μm centrifugal filter at 16,000 g. The composition was freeze-dried for 18 hours.

A control formulation was prepared by freeze drying 100 μL of 1 mg/mL bevacizumab in phosphate buffer 50 mM pH 6.2 (without silica). A bevacizumab-sucrose co-formulation control was also prepared by freeze drying 100 μL of 1 mg/mL bevacizumab and 300 μL 1 g/mL sucrose in phosphate buffer 50 mM pH 6.2.

Figure 2:
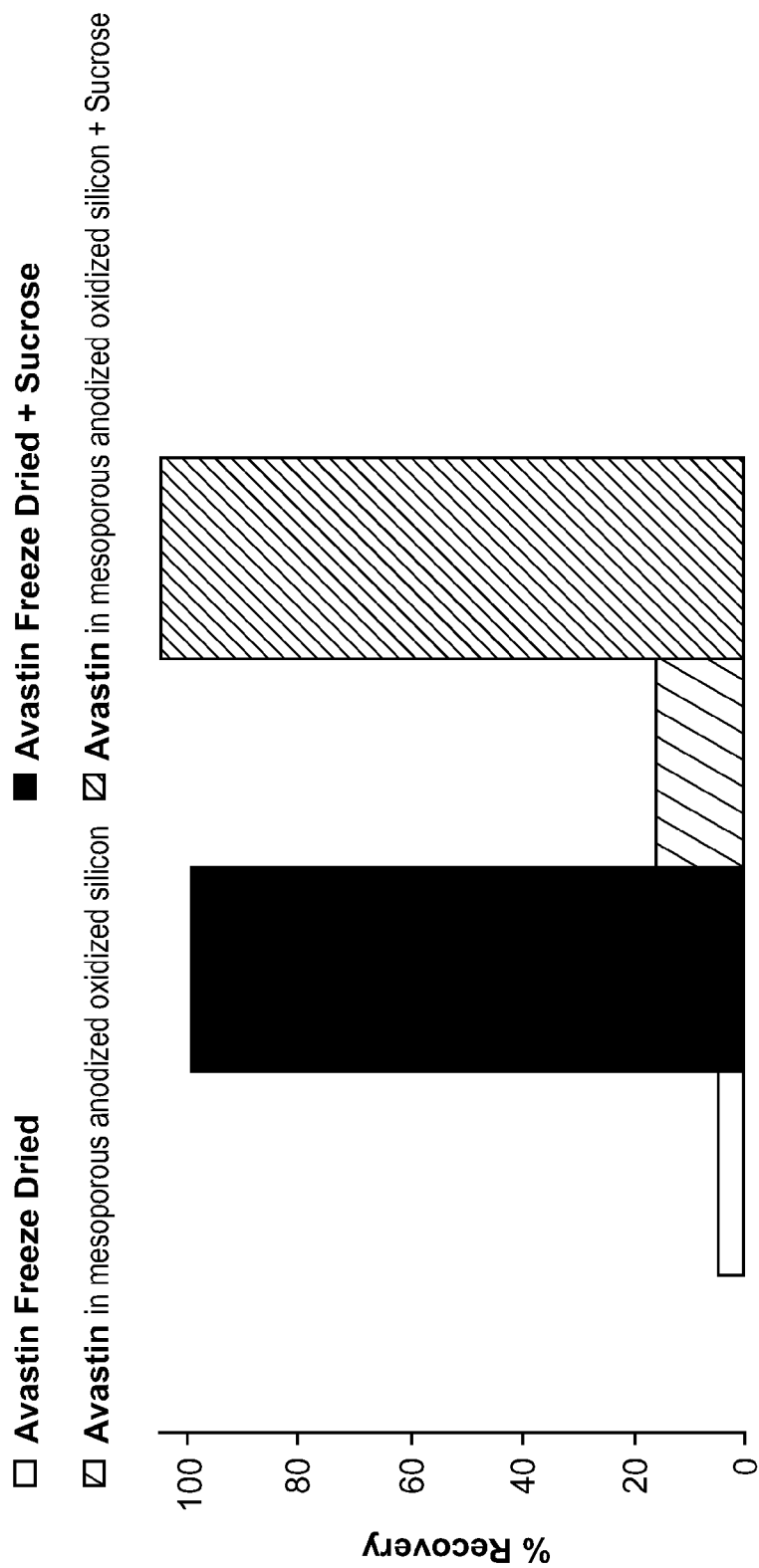
FIG. 2 shows the stability of bevacizumab after vacuum drying on mesoporous oxidized anodized silicon versus commercial freeze drying.

After drying, triplicate samples of each composition were extracted with 200 mM carbonate buffer pH 9.6 for 6 hours. After extraction the samples were centrifuged and the supernatant assayed via SEC to assay for recovery of bevacizumab. Results are shown in FIG. 2.

Example 5

Preparation of Formulations Comprising Sucrose and Mesoporous Oxidized Anodized Silicon Material Mesoporous oxidized anodized silicon material, as disclosed in U.S. Pat. No. 8,318,194 and U.S. 20120177695, was successively incubated with bevacizumab and sucrose as disclosed herein, followed by vacuum drying to remove excess water. Results are shown in FIG. 2.

Example 6

Release of Myoglobin from Polymer-Coated Particles

Figure 3:
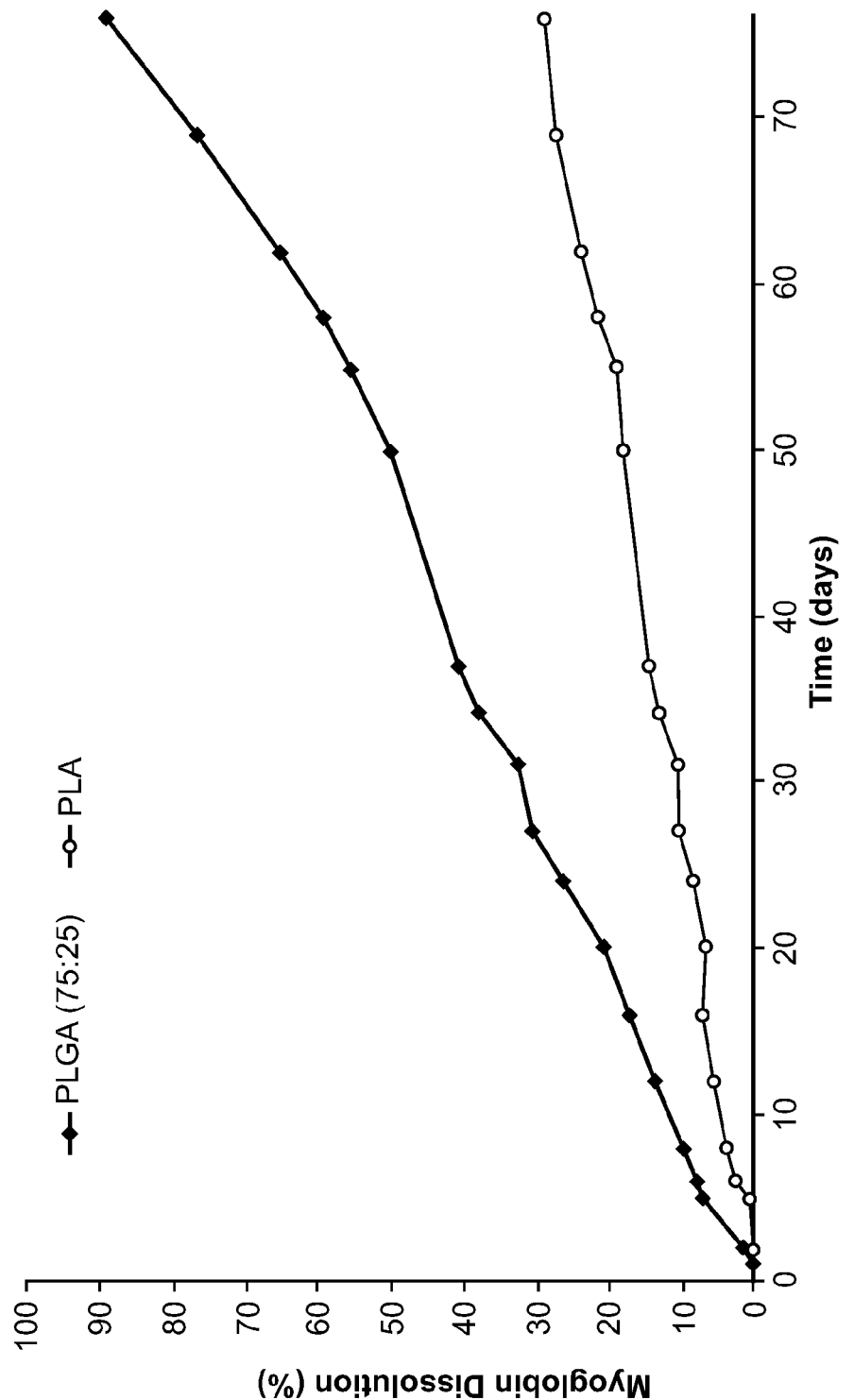
FIG. 3 shows the dissolution of myoglobin co-formulated with sucrose in coated 60 Å mesoporous oxidized anodized silicon particles.

Mesoporous oxidized anodized silicon material (60 Å) was loaded with myoglobin and sucrose in analogy to the previous examples and the loaded particles were coated with PLA or PLGA. Release of myoglobin from these coated particles is depicted in FIG. 3.

Equivalents

Those skilled in the art will recognize, or be able to ascertain using no more than routine experimentation, numerous equivalents to the compounds and methods of use thereof described herein. Such equivalents are considered to be within the scope of this invention and are covered by the following claims. Those skilled in the art will also recognize that all combinations of embodiments described herein are within the scope of the invention.

While the above described embodiments are in some cases described in terms of preferred characteristics (e.g., preferred ranges of the amount of effective agent, and preferred thicknesses of the preferred layers) these preferences are by no means meant to limit the invention. As would be readily understood by one skilled in the art, the preferred characteristics depend on the method of administration, the beneficial substance used, the shell and carrier materials used, the desired release rate and the like.

All of the foregoing U.S. patents and other publications are expressly incorporated by reference herein in each of their entireties.

We claim:

1. A method of treating or preventing a condition in a patient comprising administering to the patient a composition comprising a bioerodible porous silicon-based carrier material, wherein at least one large-molecule therapeutic agent and an amorphous sugar are disposed in pores of the carrier material.

2. The method of claim 1, wherein the composition is administered to the surface or the skin or eye of a patient.

3. The method of claim 1, wherein the composition is administered intravitreally, subcutaneously, subconjunctivally, intraperitoneally, intramuscularly or subretinally.

4. The method of claim 1, wherein the composition is administered into the eye.

5. The method of claim 4, wherein the composition is administered within the aqueous of the eye.

6. The method of claim 4, wherein the composition is administered within the vitreous of the eye.

7. The method of claim 1, wherein the condition is selected from conditions of the eye.

8. The method of claim 7, wherein the condition is selected from glaucoma, macular degeneration, diabetic macular edema, geographic atrophy and age-related macular degeneration.

9. The method of claim 1, wherein the composition releases the therapeutic agent into the eye over the course of 1 day to 6 months.

10. The method of claim 9, wherein the composition releases the therapeutic agent over the course of 1 week to 3 months.

11. The method of claim 1, wherein the porous silicon-based carrier material is contacted with a solution comprising the therapeutic agent.

12. The method of claim 1, wherein the carrier material is resorbable.

13. The method of claim 1, wherein the therapeutic agent is selected from proteins, peptides, antibodies, carbohydrates, polymers and polynucleotides.

14. The method of claim 13, wherein the therapeutic agent is an antibody.

15. The method of claim 1, wherein the amorphous sugar is selected from trehalose, trehalose dihydrate, sucrose, mannitol, sorbitol, xylitol and glycerol, or a combination thereof.

16. The method of claim 1, wherein the carrier material has a porosity in the range of about 40% to about 80%.

17. The method of claim 1, wherein the average pore size is in the range 2-50 nm.

18. The method of claim 1, wherein the average width of the walls in the carrier material which separate the pores is less than 5 nm.

19. The method of claim 1, wherein a length of the carrier material measured at its longest point is between 1 and 500 microns.

20. The method of claim 1, wherein the load level of the carrier material is less than 80% by weight based on the combined weight of the carrier material and therapeutic agent.

* * * * *